United States Patent
Mohammadi

(10) Patent No.: US 12,268,538 B2
(45) Date of Patent: Apr. 8, 2025

(54) COMPUTER TOMOGRAPH AND METHOD FOR OPERATING A COMPUTER TOMOGRAPH

(71) Applicant: ESSPEN GMBH, Erlangen (DE)

(72) Inventor: Zahra Mohammadi, Erlangen (DE)

(73) Assignee: ESSPEN GMBH, Erlangen (DE)

( * ) Notice: Subject to any disclaimer, the term of this patent is extended or adjusted under 35 U.S.C. 154(b) by 284 days.

(21) Appl. No.: 18/245,854

(22) PCT Filed: Sep. 23, 2020

(86) PCT No.: PCT/EP2020/076474
§ 371 (c)(1),
(2) Date: Mar. 17, 2023

(87) PCT Pub. No.: WO2022/058036
PCT Pub. Date: Mar. 24, 2022

(65) Prior Publication Data
US 2023/0337995 A1 Oct. 26, 2023

(30) Foreign Application Priority Data
Sep. 19, 2020 (DE) .......................... 102020124474.6

(51) Int. Cl.
*A61B 6/40* (2024.01)
*A61B 6/00* (2024.01)
(Continued)

(52) U.S. Cl.
CPC .......... *A61B 6/4014* (2013.01); *A61B 6/4021* (2013.01); *A61B 6/4435* (2013.01);
(Continued)

(58) Field of Classification Search
CPC ................ A61B 6/4014; A61B 6/4021; A61B 6/4435; A61B 6/4275; A61B 6/4405; H01J 35/30; H01J 2235/068
See application file for complete search history.

(56) References Cited

U.S. PATENT DOCUMENTS

| 4,637,040 A | | 1/1987 | Sohval | |
| 5,014,293 A | * | 5/1991 | Boyd | ..................... A61B 6/032 378/197 |

(Continued)

FOREIGN PATENT DOCUMENTS

| DE | 102010020604 A1 | 11/2011 |
| DE | 102010028438 A1 | 11/2011 |

(Continued)

OTHER PUBLICATIONS

Japanese Examination Report received for JP Application No. JP2023-517976 on Jul. 26, 2024, XX pgs.

(Continued)

*Primary Examiner* — Chih-Cheng Kao
(74) *Attorney, Agent, or Firm* — Merchant & Gould P.C.

(57) ABSTRACT

A computer tomograph includes a static radiator-detector ring, which is constructed from an odd number of radiator-detector elements, of which a single one is displaceable, with opening of the radiator-detector ring. The displaceable element the other radiator-detector elements together defining a C-shape. Each radiator-detector element has an anode arrangement for the emission of X-rays, which extends over an angle $\alpha$ of at least $0.9 \times 360°/n$ on the circumference of the radiator-detector ring. A detector is provided for detection of X-ray radiation, which extends within the same radiator-detector element over an angle $\beta$ of at least $0.95 \times 360°/n$. Each anode arrangement is part of a radiator arrangement including multiple electron emitters, in which each electron emitter is configured, in cooperation with an electrode (Continued)

arrangement, to generate a focal spot at one of at least three selectable positions on the anode arrangement.

14 Claims, 6 Drawing Sheets

(51) Int. Cl.
   *A61B 6/42* (2024.01)
   *H01J 35/30* (2006.01)

(52) U.S. Cl.
   CPC ............ *A61B 6/4275* (2013.01); *A61B 6/4405* (2013.01); *H01J 35/30* (2013.01); *H01J 2235/068* (2013.01)

(56) References Cited

U.S. PATENT DOCUMENTS

| | | | |
|---|---|---|---|
| 6,113,264 | A | 9/2000 | Watanabe |
| 7,001,045 | B2 | 2/2006 | Gregerson et al. |
| 2004/0022350 | A1 | 2/2004 | Gregerson |
| 2010/0034344 | A1 | 2/2010 | Hein |
| 2010/0150904 | A1 | 6/2010 | Cochrane |
| 2011/0280380 | A1* | 11/2011 | Maschke ............ A61B 6/4411 378/197 |
| 2017/0258427 | A1* | 9/2017 | Risher-Kelly ....... A61B 6/4441 |
| 2020/0170097 | A1* | 5/2020 | Tan ..................... H05G 1/70 |
| 2022/0338821 | A1* | 10/2022 | Mohammadi ........ A61B 6/4021 |

FOREIGN PATENT DOCUMENTS

| | | |
|---|---|---|
| DE | 102016013533 A1 | 5/2018 |
| DE | 102017008810 A1 | 3/2019 |
| DE | 102016208123 B4 | 3/2020 |
| EP | 1474040 B1 | 10/2007 |
| EP | 3569148 A1 | 11/2019 |
| EP | 3646793 A2 | 5/2020 |
| JP | S60106439 A | 6/1985 |
| JP | 2005517486 A | 6/2005 |
| JP | 2010035812 A | 2/2010 |
| JP | 2010136902 A | 6/2010 |
| WO | 2009/115982 A1 | 9/2009 |
| WO | 2010/078481 A1 | 7/2010 |
| WO | 2018008674 A1 | 1/2018 |
| WO | 2018/086737 A1 | 5/2018 |
| WO | 2018/086744 A2 | 5/2018 |
| WO | 2018/141485 A1 | 8/2018 |
| WO | 2019/057338 A1 | 3/2019 |
| WO | 2019/057339 A1 | 3/2019 |

OTHER PUBLICATIONS

International Search Report for PCT/EP2020/076474 (Jun. 21, 2021).

* cited by examiner

COMPUTER TOMOGRAPH AND METHOD FOR OPERATING A COMPUTER TOMOGRAPH

This application is a National Stage Application of PCT/EP2020/076474, filed Sep. 23, 2020, which claims benefit of Serial No. 102020124474.6, filed Sep. 19, 2020, in Germany, and which applications are incorporated herein by reference. To the extent appropriate, a claim of priority is made to each of the above disclosed applications.

BACKGROUND OF THE INVENTION

The invention relates to a computer tomograph which comprises a static radiator-detector ring, i.e., a radiator-detector ring which does not rotate during operation of the computer tomograph. The invention also relates to a method for operating such a computer tomograph.

In principle, computer tomographs can work either with rotating radiator-detector units or with stationary X-ray radiators and associated detectors. A possible design of a computer tomograph, which has a non-rotating radiator-detector unit, is described in WO 2018/086744 A2.

EP 1 474 040 B1 discloses an X-ray imaging device having a gantry frame in which an X-ray radiation source and an associated detector are rotatably mounted. A segment is detachable from the overall ring-shaped gantry in order to be able to position an object to be imaged in the central imaging area of the gantry ring. Guide devices for the radiation source and for the detector are also located in the detachable segment.

A further X-ray apparatus, which has an overall ring-shaped radiator-detector arrangement having a movable segment for the purpose of opening the ring, is described in U.S. Pat. No. 6,113,264 A. In this case, the movable segment is displaceable in the circumferential direction of the ring-shaped radiator-detector arrangement.

Documents U.S. Pat. No. 7,001,045 B2 and EP 3 646 793 A2 describe various designs of computer tomographs having ring-shaped radiator-detector assemblies that are adjustable in a variety of ways.

Computer tomographs that are movable as a whole are described, for example, in documents WO 2010/078481 A1 and DE 10 2016 208 123 B4.

DE 10 2010 028 438 A1 describes an X-ray device designed as a C-arm device, which has carbon nanotubes as electron emitters. Scanning trajectories, which are described in detail in DE 10 2010 028 438 A1, are implementable with the aid of multiple X-ray radiation sources arranged differently in space.

SUMMARY OF THE INVENTION

The invention is based on the object of specifying possibilities for X-ray imaging using a static radiator-detector ring which are refined over the prior art, wherein good handling and outstanding quality of the imaging are provided with an apparatus design that is not excessively complicated.

This object is achieved according to the invention by a computer tomograph having the features of claim 1. The object is also achieved by a method for operating a computer tomograph as claimed in claim 11. The embodiments and advantages of the invention explained below in connection with the operating method also apply to the device, i.e., the computer tomograph, and vice versa.

The computer tomograph comprises a static radiator-detector ring, which is constructed from an odd number n of radiator-detector elements, of which a single one is displaceable, with opening of the radiator-detector ring, in relation to the other radiator-detector elements describing a C-shape together, wherein each radiator-detector element has an anode arrangement provided for the emission of X-rays, which extends over an angle $\alpha$ of at least $0.9 \times 360°/n$ on the circumference of the radiator-detector ring, and a detector provided for the detection of X-ray radiation, which extends within the same radiator-detector element over an angle $\beta$ of at least $0.95 \times 360°/n$, and wherein each anode arrangement is part of a radiator assembly comprising multiple electron emitters, in which each electron emitter is designed, in cooperation with an electrode arrangement, to generate a focal spot at one of at least three selectable positions on the anode arrangement. The optionally settable positions of the focal spot that can be generated using the same electron emitter are arranged adjacent to one another, in particular in the circumferential direction of the radiator-detector ring, i.e., in different angular positions around the central axis of the computer tomograph, in particular are arranged equidistantly. Switching between different focal spot positions by gradually changing the setting of an electrode arrangement is referred to as beam toggling.

The operating method according to the application is based on the assumption that a computer tomograph is used which comprises a non-rotating radiator-detector ring which is constructed from an odd number of radiator-detector elements, i.e, segments, of which a single segment is designed to open the radiator-detector ring, wherein a plurality of electron emitters is arranged both in the fixed radiator-detector elements and in the radiator-detector element to be opened, which are each designed, with the aid of electrodes influencing electron beams, to generate a focal spot having a variable position on an anode associated with the radiator-detector element, so that the total number of possible focal spot positions corresponds to a multiple of the number of electron emitters, and wherein the maximum angular distance between two focal spot positions arranged adjacent to one another within the same radiator-detector element is less than the minimum angular distance between focal spot positions of two adjacent radiator-detector elements. The operating method comprises the following steps:

Positioning the radiator-detector ring around an examination object, wherein the radiator-detector ring is initially open and is closed at the latest in a position intended for carrying out an X-ray examination, Directing a fan-shaped X-ray beam, which originates from a first focal spot, onto the examination object, wherein X-ray radiation is detected by detectors of at least two radiator-detector elements, Generating a second focal spot, which is offset by a first differential angle in relation to the first focal spot on the circumference of the radiator-detector ring and is not necessarily arranged directly adjacent to the first focal spot, Generating further focal spots, which are each offset on the circumference of the radiator-detector ring in relation to the previous focal spot by a differential angle, wherein the differential absolute value between two successive differential angles is less than the difference between the minimum angular distance between focal spot positions in adjacent radiator-detector elements and the maximum angular distance between two adjacent focal spot positions within the same radiator-detector element.

The invention is based on the consideration that a computer tomograph whose radiator-detector ring can be opened offers advantages over conventional computer tomographs having a permanently closed radiator-detector ring when preparing X-ray recordings. For example, the radiator-detector ring to be opened can be pushed in the open state from the side over a table on which the patient is lying. Despite the possibility of opening the radiator-detector ring, a mass-saving construction with a high number of focal spot positions at the same time is favored by the fact that different focal spot positions are settable alternately for each electron emitter. Overall, the anodes, which are positioned on the circumference of the radiator arrangement, occupy at least 90% of the circumference, i.e., 324°. Because of the odd number of radiator-detector elements, a joint between two radiator-detector elements is never exactly diametrically opposite to another such joint. If there is a focal spot in the edge region of a radiator-detector element, i.e., near a joint, X-ray radiation originating from this focal spot are incident on two circumferentially adjacent X-ray detectors, which are, for example, photon-counting detectors. In particular, the use of line detectors comes into consideration. In this context, reference is made to WO 2019/057339 A1. In general, scintillation detectors, which can be of any shape, can also be used as X-ray detectors. In any case, in comparison to the anodes of the radiator-detector ring, the detectors extend over an even greater angle, namely over at least 95% of the circumference, i.e., over an angle of in total at least 342°, divided over the individual segments of the radiator-detector ring.

In comparison to the minimum angular distance that can exist between focal spot positions in adjacent radiator-detector elements, the possible focal spot positions within the same radiator-detector element are staggered much more closely. If all possible focal spot positions in the circumferential direction of the radiator-detector ring were selected in succession, a much larger jump in the angular setting would occur regularly at a number of small angular distances, namely when changing from one radiator-detector element to the next radiator-detector element. An equalization of the angular distances between one focal spot position and the next focal spot position in the time sequence is provided by the operating method according to the application. By successively switching between different focal spot positions, multiple revolutions around the central axis of the radiator-detector ring can be described, wherein all possible focal spot positions have only been assumed after multiple revolutions. In particular, with each individual revolution, focal spots are generated in mutually deviating settings of the electrodes influencing the electron beams. This can mean, for example, that during a virtual X-ray source revolution, a first electrode arrangement is set in such a way that an electron beam remains in a central, neutral alignment, while a second electrode arrangement belonging to another electron emitter ensures that the corresponding electron beam is deflected in a certain direction in comparison to its neutral alignment, which is accompanied by a shift of the focal spot on the circumference of the radiator-detector ring.

Possibilities for successive adjustment of the angle setting of the X-ray radiation, i.e., switching between different possible focal spot positions, during operation of the computer tomograph are explained hereinafter using a simplified numerical example:

A radiator-detector ring is constructed from only three radiator-detector elements, each of which extends over an angle of approximately 120°. A junction between the first and the third radiator-detector element is in the 0° position. The centers of the three segments—viewed in the circumferential direction of the radiator-detector ring—are therefore at 60°, 180°, and 300°.

For the sake of simplicity, it is assumed that each radiator-detector element has only two electron emitters, wherein the electron beam originating from an emitter can be directed at the associated anode arrangement in three different ways: The electron beam is directed at the anode either with a central orientation or with clockwise deflection or with counterclockwise deflection, wherein the direction specifications of the deflection relate to the circumferential direction of the radiator-detector ring.

Equal distances between the possible focal spot positions within the first radiator-detector element are given, for example, with the following focal spot positions: 20°, 36°, 52°, 68°, 84°, 100°. The first three values are assigned to the first electron emitter and the values 68°, 84°, 100° to the second electron emitter. The central alignments of the electron beams correspond to the focal spot positions 36° (first electron emitter) and 84° (second electron emitter). In the numerical example discussed, which is based on a very small number of electron emitters, the electron beams can be deflected in comparison to the respective mean alignment in such a way that the focal spot positions result, which are offset by ±16° compared to the focal spot position that results at the center alignment of the electron beam. There are thus always angular distances of 16° between a focal spot position located within the first radiator-detector element and the next possible focal spot position within the same radiator-detector element.

Analogously, focal spot positions are selectable at 140°, 156°, 172°, 188°, 204°, 220° within the second radiator-detector element and focal spot positions at 260°, 276°, 292°, 308°, 324°, 340° are selectable within the third radiator-detector element. The first radiator-detector element represents the segment of the radiator-detector ring to be opened. The second radiator-detector element is permanently connected to the third radiator-detector element. Notwithstanding the fact that the radiator-detector elements differ from one another in terms of their mechanical function, all radiator-detector elements are constructed identically in terms of their X-ray function, in particular the arrangement of the X-ray sources, i.e., focal spots on the anodes, and the X-ray detectors. When carrying out and evaluating a computer tomographic, i.e., X-ray examination, it is therefore not necessary to consider the extent to which one radiator-detector element is adjustable in relation to the other radiator-detector elements.

In order to ensure the desired adjustability of one of the radiator-detector elements and at the same time to design all radiator-detector elements in the same way in terms of their X-ray function, the available 120° installation space within each radiator-detector element can only be partially utilized by the respective anode arrangement. There is therefore an angular distance between the outermost possible focal spot position of one radiator-detector element and the focal spot position of the next radiator-detector element that is the smallest distance away from it, which is significantly larger than the angular distances between the focal spot positions within the same radiator-detector element. In the present case, the following minimum angular distances between focal spot positions of different radiator-detector elements across all elements are provided: between the first and the third element (20° or 340°) an angular distance of 40° and between the first and the second element (100° or 140°) as well as between the second and the third element (220° or 260°), also in each case an angular distance of 40°.

If all possible focal spot positions were set in succession in a clockwise (or counterclockwise) direction, which simulates a mechanical rotation of an X-ray source around the longitudinal axis of the computer tomograph, five angle changes of 16° each would always be followed by an angle change of 40°, which is again followed by five jumps of 16°.

This unevenness in the angle jumps can be remedied by using a novel scheme, according to which different focal spot positions are set in succession:

Beginning with the first possible position of a focal spot clockwise, i.e., the 20° position, six virtual revolutions are started, wherein in the simplified example only three focal spot positions are selected in succession in each revolution, which are offset by an average of 120° from one another. In detail, a possible sequence of focal spot positions is: 20°, 140°, 276°, 52°, 172°, 308°, 84°, 204°, 340°, 100°, 220°, 324°, 68°, 188°, 292°, 36°, 156°, 260°, which means that each of the 18 possible focal spot positions was selected exactly once after the six virtual revolutions. The average angular distances of 120° are not deviated from by more than 16° upwards or downwards, wherein the angular distance of 120° is given eight times and an angular distance of 136° or 104° is given five times each and the value 104° never follows the value 136° (or vice versa). This also applies to a new start of the six virtual revolutions, i.e., for the change from the 260° position to the 20° position, which corresponds to a differential angle of exactly 120°.

In the simplified example under consideration, only three different values appear as differential angles, namely the values 104°, 120°, 136°, wherein the differential absolute value between two successive differential angles, i.e., the absolute value of 0° or 16°, is less than the angular distance between the focal spots located closest to one another of two radiator-detector elements. In the present case, the differential absolute value is even less than half of the stated angular distance of 40° extending across a segment boundary. If one subtracts from this segment-spanning angular distance the uniform angular distance within the segments of 16° in the example explained, the result is a difference of 24°, which is still greater than the largest differential absolute value occurring between chronologically successive differential angles. Despite the uneven distribution of the focal spots on the circumference of the radiator-detector ring due to the segmentation of the radiator-detector ring and its opening mechanism, fluoroscopy of an examination object using X-ray radiation in the form of fan-shaped beams each originating from a focal spot, which fluoroscopy is performed in comparatively equal angle jumps, which simulate a rotation of an X-ray source, is possible.

Each focal spot is located on an anode arrangement, which may include either a single or multiple liquid-cooled or uncooled anodes per X-ray tube. For example, anodes are used as are described in DE 10 2017 008 810 A1. Independently of the design of the anodes, the computer tomograph can be designed in such a way that the radiator-detector elements simultaneously generate two or more mutually offset focal spots on the circumference of the radiator-detector ring. The case of exactly two focal spots and correspondingly two X-ray beams, using which a volume of interest is examined, is also referred to as a stereo tactic of X-ray imaging.

With regard to the design of the cathodes, which are used as electron emitters of the computer tomograph, options can be selected, for example, which are selected in WO 2019/057338 A1, which claims the priority of the cited patent application DE 10 2017 008 810 A1.

Options for activation, which can also be used in the present case, are described in WO 2019/042587 A2, for example. When producing the cathodes designed to emit electrons, it is possible to use any of the solutions mentioned in documents WO 2018/086737 A1 and WO 2018/141485 A1, for example.

Overall, the X-ray tubes of the computer tomograph can be designed to generate a sequence of X-ray pulses that differ from one another with regard to a wide variety of parameters, among others duration, intensity, and X-ray dose of the individual pulses and the frequency of the X-ray radiation. For this purpose, among other things, a variation of the voltage applied to an anode and a variation of the electron currents originating from the cathodes can be provided. These possible variations relating to the X-ray sources show their advantages particularly in combination with photon-counting detectors, which are suitable for distinguishing different X-ray frequencies, i.e., are predestined for multi-energy and multi-dose operating modes.

The computer tomograph can be a mobile or a stationary X-ray device. The computer tomograph is suitable, among other things, for examinations in the thoracic area.

BRIEF DESCRIPTION OF THE DRAWINGS

In the following, an exemplary embodiment of the invention will be described in greater detail with reference to a drawing. In the figures.

DETAILED DESCRIPTION OF THE PREFERRED EMBODIMENT

Figure 1:
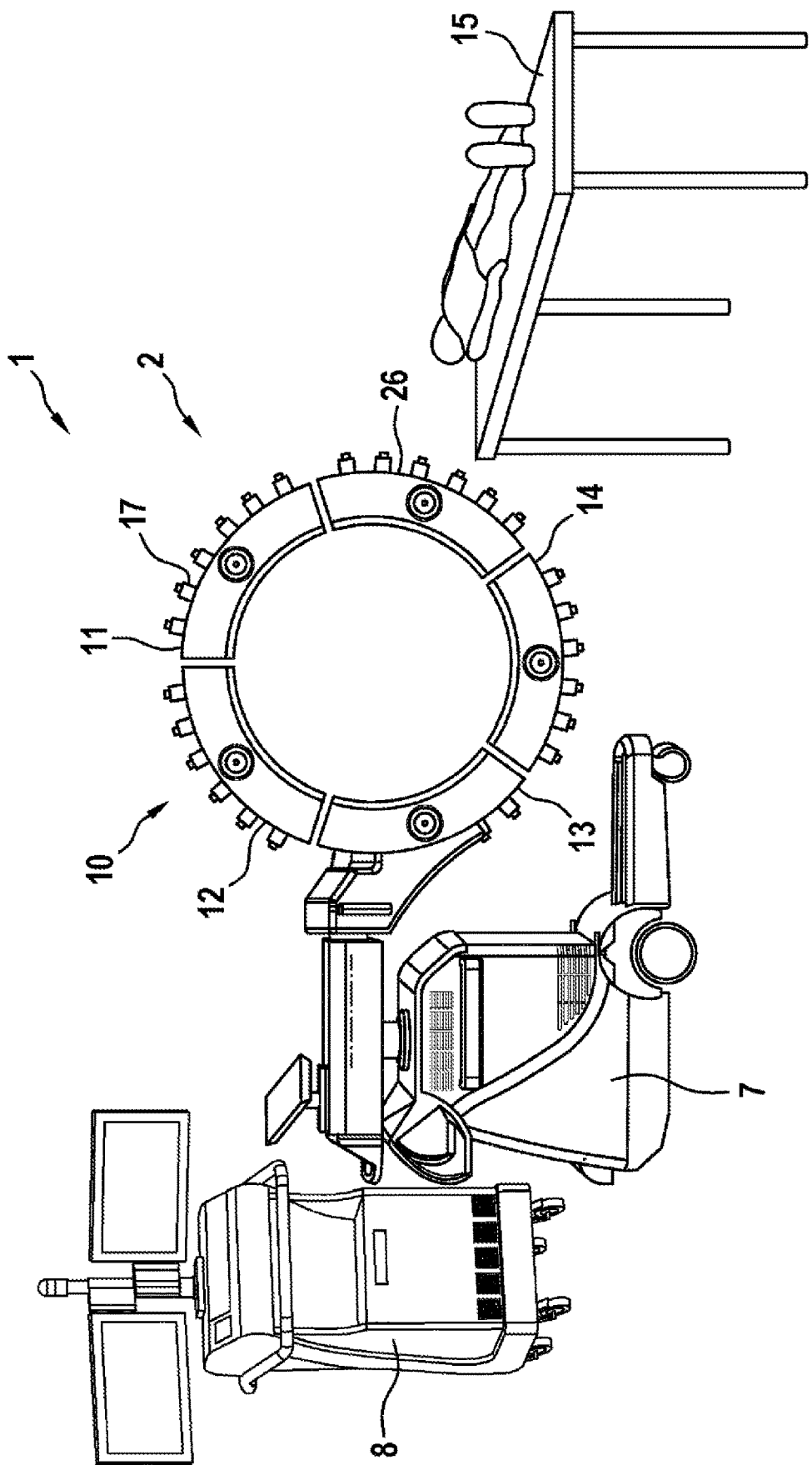
FIG. 1 shows a computer tomograph in an overview illustration.

A computer tomograph identified overall by the reference sign 1 comprises a fixed gantry 2, wherein the term "fixed" is to be understood to mean that there is no rotation of an radiator-detector unit around the central axis MA of the gantry 2 when obtaining X-ray images. Rather, with the aid of X-ray tubes 3 distributed around the entire circumference of the gantry 2 and associated X-ray detectors 4, fan-shaped bundles of X-ray radiation RS can be generated, which each originate from a focal spot BF on an anode 6 of the X-ray tube 3. The individual X-ray tubes 3 each have multiple cathodes 5, 25 assigned as electron emitters. In the exemplary embodiment outlined, each X-ray tube 3 has a single, elongated anode 6 which, in this case, is also considered an anode arrangement 9. Alternatively, the anode arrangement 9 of an X-ray tube 3 can be constructed from a plurality of anodes 6.

The gantry 2 is attached to a movable frame 7 in a manner adjustable in multiple ways. Among other things, tilting of the gantry 2 around a horizontal tilting axis orthogonally intersecting the central axis MA is possible. Likewise, the gantry 2 can be displaced in the longitudinal direction of the horizontally arranged central axis MA. In addition, limited adjustments of the gantry 2 in its circumferential direction are also possible. There is also the possibility of raising or lowering the entire gantry 2. In the exemplary embodiment, a separate operating and evaluation unit 8 is present in addition to the movable frame 7. A structural combination of movable frame 7 and operating and evaluation unit 8 is also conceivable.

Figure 2:
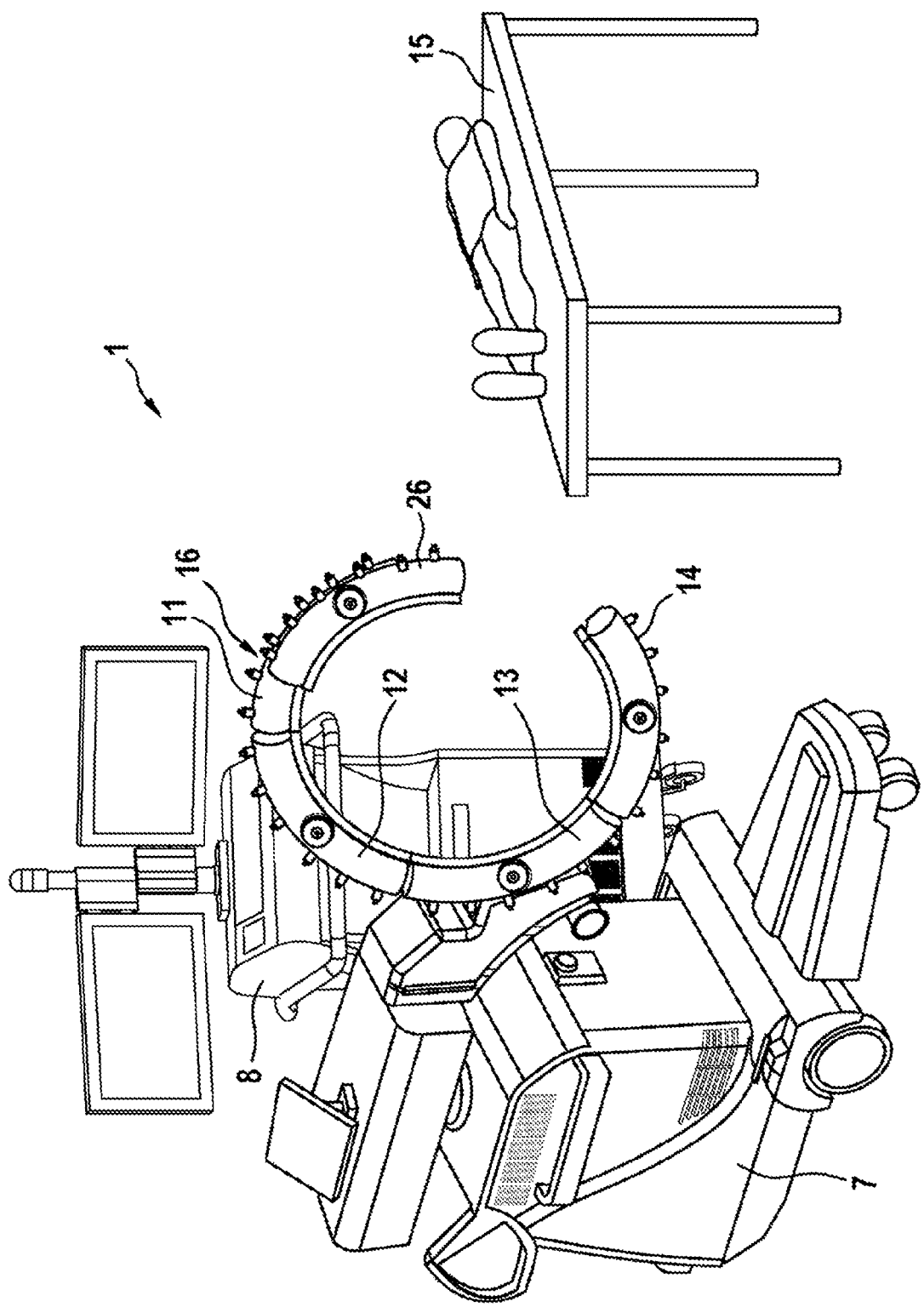
FIG. 2 shows, in a representation analogous to FIG. 1, the computer tomograph having open radiator-detector ring.
Figure 3:
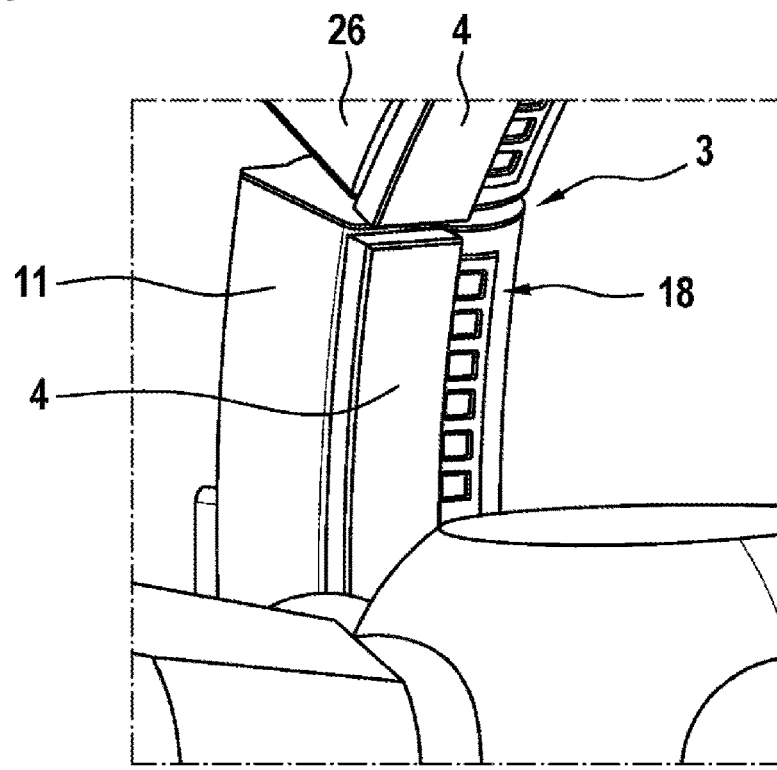
FIGS. 3 and 4 show, in different enlargements, details of the computer tomograph.

A housing enclosing the gantry 2 is not provided. Rather, the entire gantry 2 is constructed as an radiator-detector ring 10, which is formed from a total of five radiator-detector elements 11, 12, 13, 14, 26. In this case, the radiation detector elements 11, 12, 13, 14 represent fixed elements that are rigidly connected to one another, whereas the radiator element 26 is displaceable in order to open the radiator-detector ring 10. The opening takes place in order to enclose a patient table 15 using the radiator-detector ring 10. The opening mechanism is constructed as a slide mechanism 16. Starting from the closed radiator-detector ring 10, as shown in FIG. 1, the radiator-detector element 26 is initially displaced somewhat in the longitudinal direction of the center axis MA, i.e., raised out of the radiator-detector ring 10. In this state, in which the radiator-detector element 26 is positioned adjacent to the C-shaped arrangement of the remaining radiator-detector elements 11, 12, 13, 14, the radiator-detector element 26 can be displaced in the circumferential direction of the C-shaped arrangement 11, 12, 13, 14, whereby the opening at the circumference of the radiator-detector ring 10, as shown in FIG. 2, is released. Tilting of the radiator-detector element 26 in relation to the remaining radiator-detector elements 11, 12, 13, 14 does not occur at any time. Due to the lack of tilting mechanisms, with regard to the radiator-detector element 26, the available space, which extends over a 72° angle on the circumference of the radiator-detector ring 10, can largely be used for the installation of X-ray components, which will be discussed in more detail hereinafter.

Figure 4:
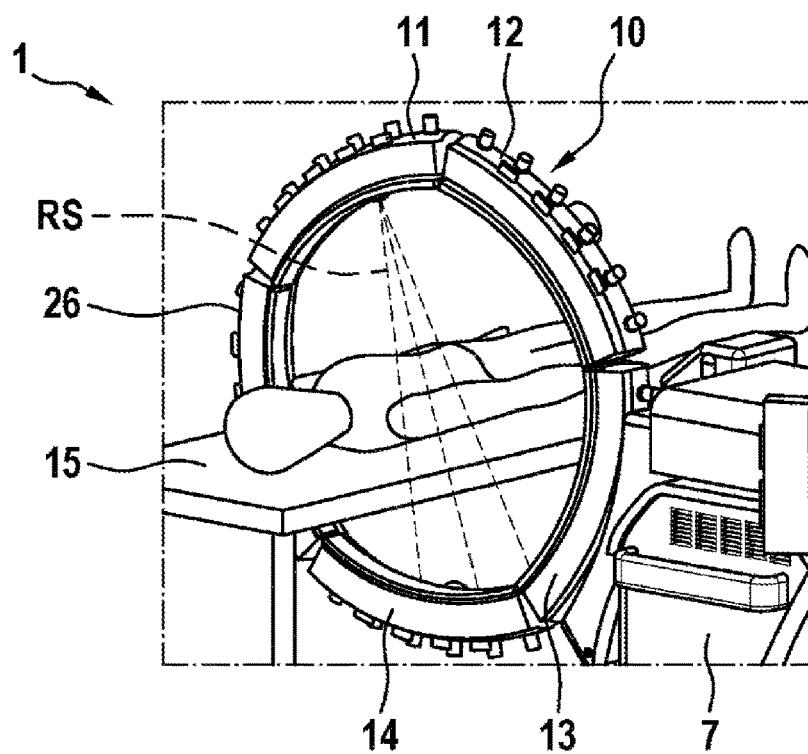
Figure 5:
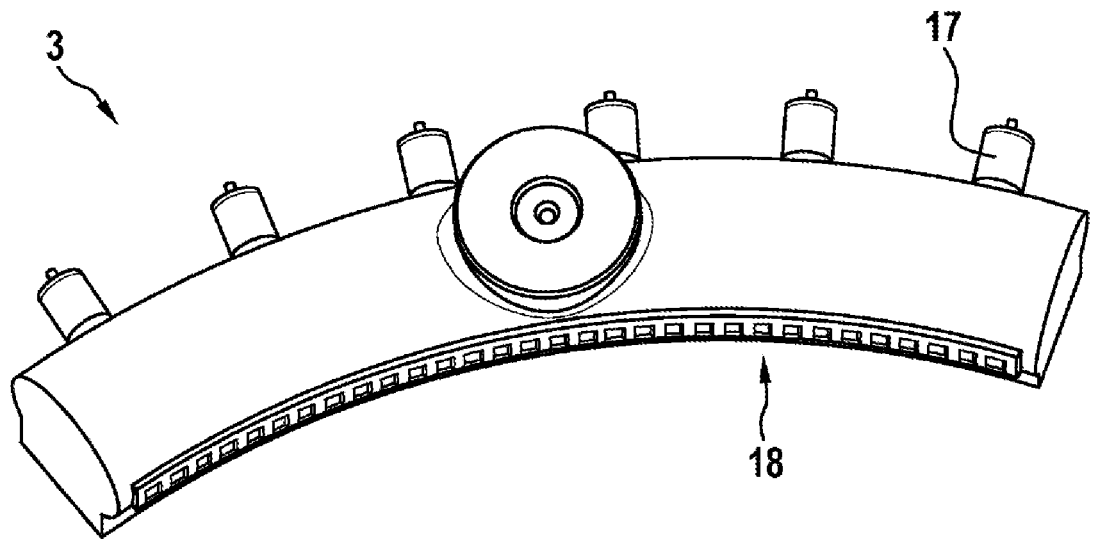
FIGS. 5 to 7 show an X-ray tube of the computer tomograph.
Figure 6:
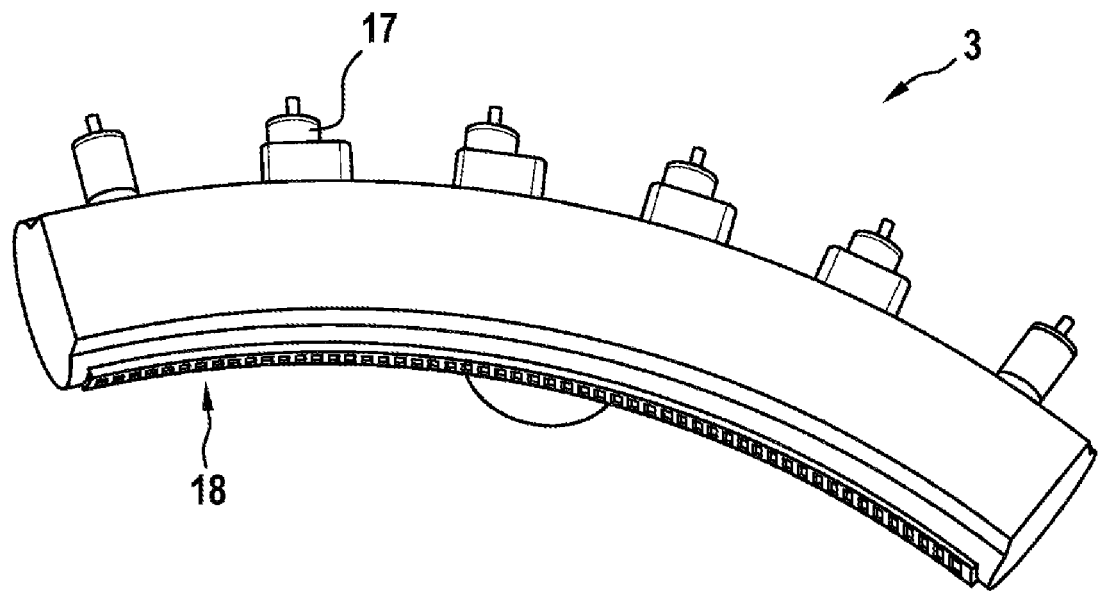
Figure 7:
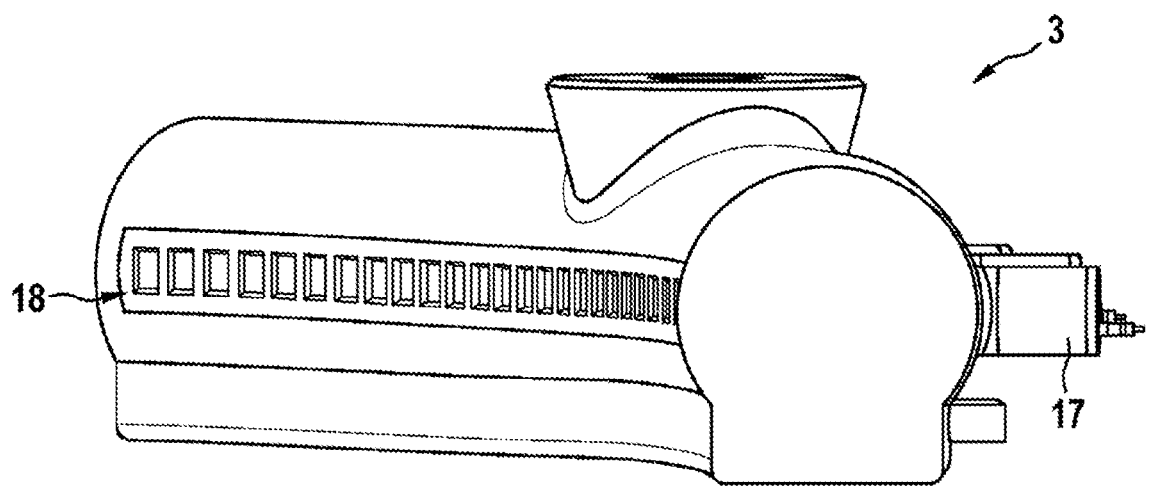
Figure 8:
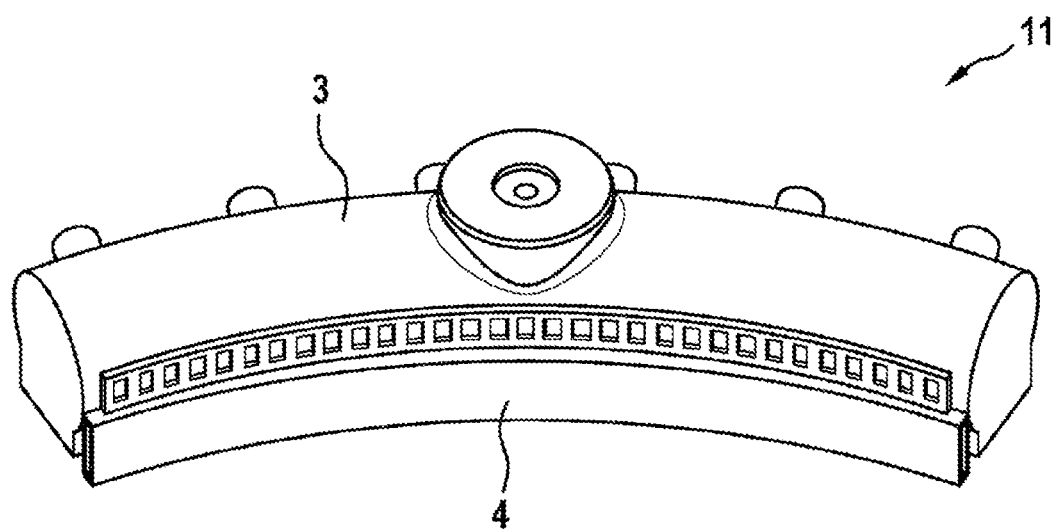
FIG. 8 shows a radiator-detector element of the computer tomograph constructed from an X-ray tube and associated detector.

With regard to the arrangement of X-ray components, the displaceable radiator-detector element 26 does not differ from the fixed radiator-detector elements 11, 12, 13, 14. Each radiator-detector element 11, 12, 13, 14, 26 has a uniform structure shown in FIGS. 5 to 8. Fittings of the X-ray tubes 3 are denoted by 17. Radiator assemblies 18 of the X-ray tubes 3 emit X-ray radiation RS in such a way that, as illustrated in FIG. 4, two of the five radiator-detector elements 11, 12, 13, 14, 26—more precisely: their detectors 4—are struck. Because of the odd number of the radiator-detector elements 11, 12, 13, 14, 26, a joint between two radiator-detector elements 11, 12, 13, 14, 26 is never exactly diametrically opposite to another such joint.

In each X-ray tube 3 there is an emitter assembly 19 for generating electron beams ES, which strike the anode arrangement 9 and thus generate the focal spot BF. The focal spot BF does not necessarily have an approximately punctiform shape. Rather, in a way that is known in principle, elongated focal spots BF can also be generated, for example, wherein the position of the focal spot BF is to be understood in each case as the position of its center point.

In the exemplary embodiment, the emitter assembly 19 comprises different cathodes 5, 25 in order to generate X-ray radiation of different doses and/or wavelengths. In any case, electrons are extracted from the cathode 5, 25 with the aid of an extraction grid 20, wherein the electron beam ES is deflectable in a defined manner with the aid of an electrode arrangement 21 which comprises multiple electrodes 22, 23. A plurality of cathodes 5, 25 are arranged together on a circuit board 24.

The entire anode arrangement 9 interacting with the emitter assembly 19 of an X-ray tube 3 extends at the circumference of the radiator-detector ring 10 over an angle $\alpha$ which is significantly less than 72°. An angle $\beta$, which indicates the extension of the X-ray detector 4 on the circumference of the radiator-detector ring, is significantly closer to 72°. In other words: the gaps formed between the individual X-ray detectors 4 on the circumference of the radiator-detector ring 10 are significantly narrower than the gaps formed between the radiator arrangements 18. A large number of possible focal spot positions extend within the X-ray tube 3 over an angle $\gamma$ which is less than the angle $\alpha$.

Figure 9:
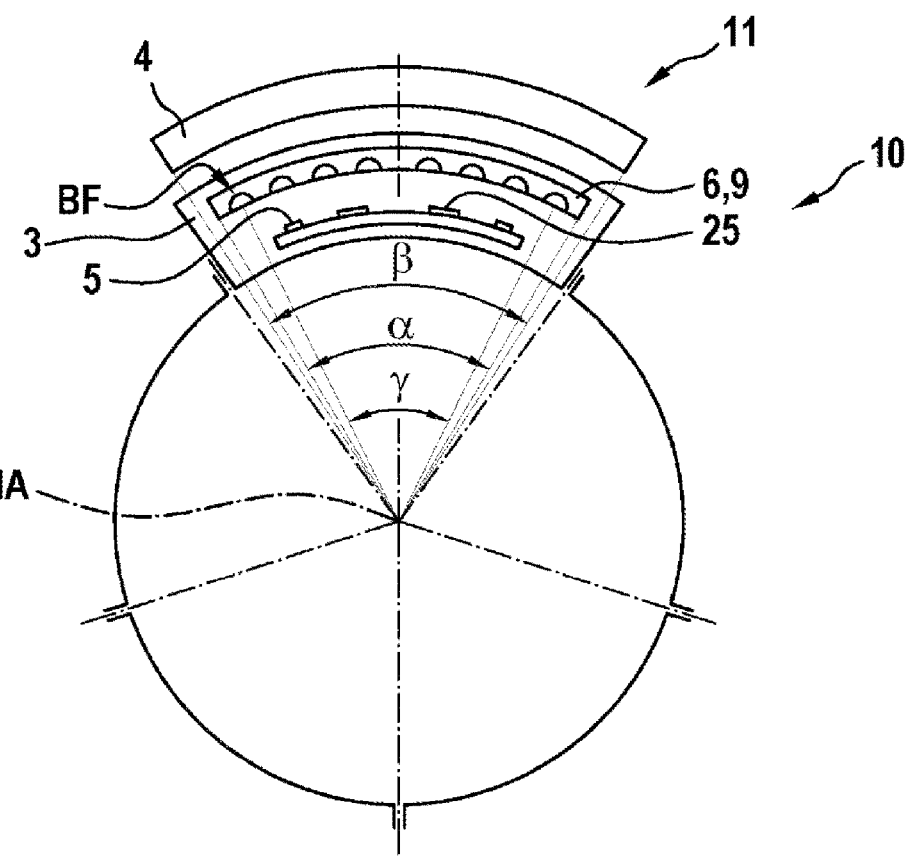
FIGS. 9 and 10 show schematic representations of details of the computer tomograph.
Figure 10:
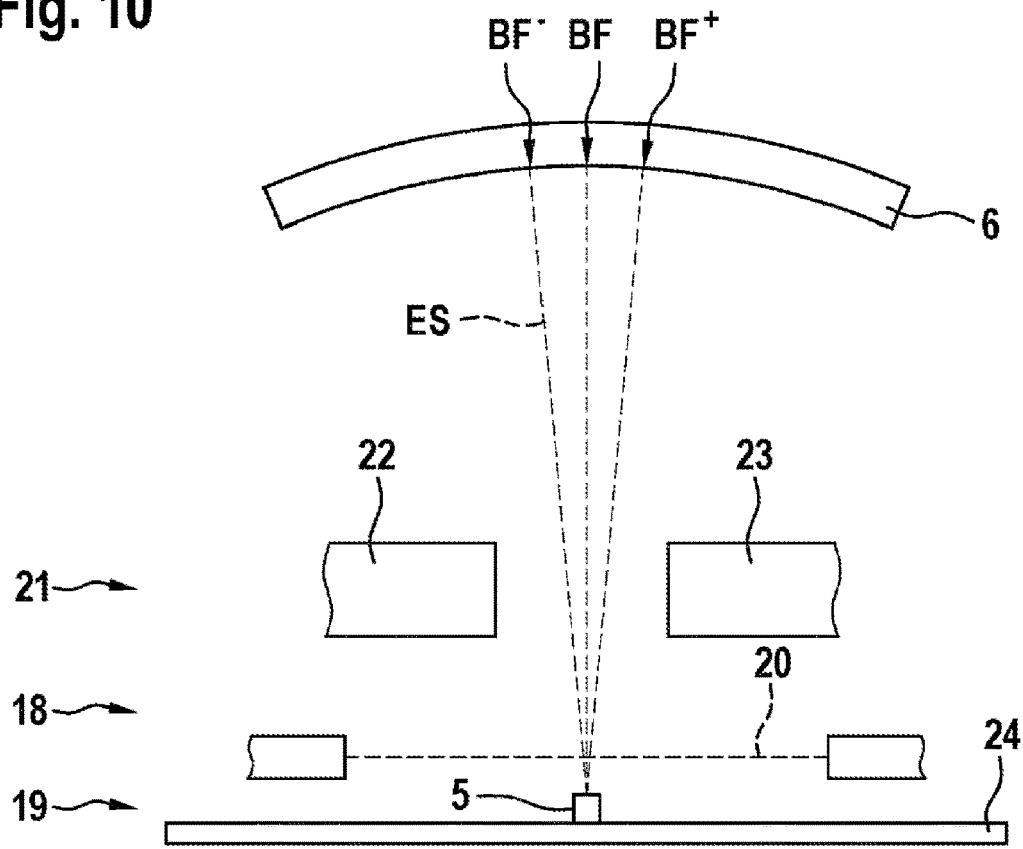

The electrode arrangement 21 is designed to selectively direct the electron beam ES onto the focal spot BF or onto a focal spot $BF^+$, $BF^-$ that is offset in comparison thereto in the circumferential direction of the radiator-detector ring 10. With respect to the arrangement according to FIGS. 9 and 10, the focal spot BF is deflected clockwise in relation to the focal spot BF and the focal spot $BF^-$ is deflected counter-clockwise. The deflections of the electron beam ES, which mean an offset of the focal spot BF, are also referred to as beam toggling and enable focal spots $BF^-$, BF, $BF^+$ to be placed particularly closely staggered on the circumference of the radiator-detector ring 10. A total number of several hundred focal spot positions, which corresponds to a multiple of the number of electron emitters 5, 25, is achievable.

LIST OF REFERENCE SIGNS 1 computer tomograph
2 gantry
3 X-ray tube
4 X-ray detector
5 cathode of the first type, electron emitter
6 anode
7 movable frame
8 operating and evaluation unit
9 anode arrangement
10 radiator-detector ring
11 first fixed radiator-detector element
12 second fixed radiator-detector element
13 third fixed radiator-detector element
14 fourth fixed radiator-detector element
15 patient bed
16 sliding mechanism
17 fitting
18 radiator assembly
19 emitter assembly
20 extraction grid
21 electrode arrangement
22 electrode
23 electrode
24 circuit board
25 cathode of the second type, electron emitter
26 displaceable radiator-detector element
$\alpha$ angle over which the anode arrangement of a radiator-detector element extends
$\beta$ angle over which the detector of a radiator-detector element extends
$\gamma$ angular range in which the possible focal spots of an anode arrangement are located
BF focal spot (general)
$BF^+$, $BF^-$ focal spot, generated by means of an electron emitter (in the middle position and in two positions offset in the circumferential direction of the radiator-detector ring)
ES electron beam
MA central axis
RS X-ray radiation

The invention claimed is:

1. A computer tomograph, comprising a static radiator-detector ring, which is constructed from an odd number (n) of radiator-detector elements, of which a single radiator-detector element is displaceable, with opening of the radiator-detector ring, the displaceable radiator-detector element with the remaining radiator-detector elements together defining a C-shape, wherein each radiator-detector element has an anode arrangement provided for the emission of X-rays, which extends over an angle α of at least 0.9×360°/n on a circumference of the radiator-detector ring, and a detector provided for detection of X-ray radiation, which extends within the same radiator-detector element over an angle β of at least 0.95×360°/n, and wherein each anode arrangement is part of a radiator arrangement comprising a plurality of electron emitters, in which each electron emitter is configured, in cooperation with an electrode arrangement, to generate a focal spot at one of at least three selectable positions on the anode arrangement.

2. The computer tomograph as claimed in claim 1, wherein the radiator-detector element displaceable in relation to the remaining radiator-detector ring is displaceable in an axial direction of the radiator-detector ring and, in an axially displaced state, is slidable in a tangential direction along the radiator-detector elements arranged overall in a C-shape.

3. The computer tomograph as claimed in claim 1, wherein the radiator-detector elements have emitters configured for field emission of electrons, in particular emitters comprising carbon nanotubes.

4. The computer tomograph as claimed in claim 3, wherein each radiator-detector element has at least one emitter of a first type and at least one emitter of a second type.

5. The computer tomograph as claimed in claim 4, wherein the different emitter types within a radiator-detector element differ from one another with regard to materials and/or geometry.

6. The computer tomograph as claimed in claim 3, wherein the radiator-detector elements are configured for switching between different X-ray frequencies and/or X-ray doses, wherein each focal spot is equally selectable as a source of all settable X-ray frequencies and X-ray doses.

7. The computer tomograph as claimed in claim 1, wherein the radiator-detector ring is attached in an adjustable manner to a movable device frame.

8. The computer tomograph as claimed in claim 1, wherein the radiator-detector ring comprises at least five radiator elements and at most nine radiator elements, wherein all radiator-detector elements, including the displaceable radiator-detector element, cover angular ranges of equal size.

9. The computer tomograph as claimed in claim 1, wherein between the most distant focal spots of the same anode arrangement, an angle γ of at least 0.85×α is enclosed on the circumference of the radiator-detector ring and from each of the possible focal spot positions, a fan-shaped X-ray beam is alignable on at least two radiator-detector elements diametrically opposite to the focal spot on the radiator-detector ring.

10. The computer tomograph as claimed in claim 1, wherein the radiator-detector elements are configured to simultaneously generate at least two mutually offset focal spots on the circumference of the radiator-detector ring.

11. The computer tomograph as claimed in claim 1, wherein the radiator-detector elements have emitters comprising carbon nanotubes configured for field emission of electrons.

12. A method for operating a computer tomograph, which comprises a non-rotating radiator-detector ring which is constructed from an odd number (n) of radiator-detector elements, of which a single radiator-detector element is configured to open the radiator-detector ring, wherein a plurality of electron emitters is arranged both in the fixed radiator-detector elements and in the radiator-detector element to be opened, which are each configured, with the aid of electrodes influencing electron beams, to generate a focal spot having a variable position on an anode associated with the radiator-detector element, so that a total number of possible focal spot positions corresponds to a multiple of the number of electron emitters, and wherein the maximum angular distance between two focal spot positions arranged adjacent to one another within the same radiator-detector element in the circumferential direction of the radiator-detector ring is less than the minimum angular distance between focal spot positions of two adjacent radiator-detector elements, comprising the following steps:

positioning the radiator-detector ring around an examination object, wherein the radiator-detector ring is closed, at the latest, in a position provided for carrying out an X-ray examination, directing a fan-shaped X-ray beam, which originates from a first focal spot, onto the examination object, wherein X-ray radiation is detected by detectors of at least two radiator-detector elements, generating a second focal spot, which is offset by a first differential angle in relation to the first focal spot on the circumference of the radiator-detector ring, generating further focal spots, which are each offset on the circumference of the radiator-detector ring in relation to the previous focal spot by a differential angle, wherein a differential absolute value between two successive differential angles is less than a difference between a minimum angular distance between focal spot positions in adjacent radiator-detector elements and a maximum angular distance between two adjacent focal spot positions within the same radiator-detector element.

13. The method as claimed in claim 12, wherein multiple revolutions around the central axis of the radiator-detector ring are defined by successive switching between different focal spot positions, wherein all possible focal spot positions have only been assumed after a plurality of revolutions.

14. The method as claimed in claim 13, wherein focal spots are generated in mutually differing settings of different electrodes influencing electron beams during each individual revolution.

* * * * *